United States Patent [19]

Izatt et al.

[11] Patent Number: 4,785,185
[45] Date of Patent: Nov. 15, 1988

[54] SUBMILLIMETER LASER MEASUREMENT OF WATER OR FILLER CONTENT OF SHEETS AND BANDS OF DIELECTRIC MATERIAL

[75] Inventors: Jerald R. Izatt, Northport, Ala.; Russell Boulay, Cap-Rouge, Canada

[73] Assignee: The University of Alabama, Tuscaloosa, Ala.

[21] Appl. No.: 924,273

[22] Filed: Oct. 29, 1986

Related U.S. Application Data

[63] Continuation-in-part of Ser. No. 730,734, May 6, 1985.

[51] Int. Cl.⁴ ............................................. G01F 23/00
[52] U.S. Cl. .............................. 250/358.1; 250/359.1; 250/339
[58] Field of Search ..................... 250/341, 339, 358.1, 250/359.1

[56] References Cited

U.S. PATENT DOCUMENTS 3,597,616  8/1971  Brunton et al. ...................... 250/341
4,450,356  5/1984  Murray et al. ....................... 250/339

Primary Examiner—Carolyn E. Fields
Assistant Examiner—David P. Porta
Attorney, Agent, or Firm—Oblon, Fisher, Spivak, McClelland & Maier

[57] ABSTRACT

A method and apparatus for detecting the moisture or filler content of dielectric material is disclosed which utilizes a submillimeter laser source of radiation scanned across the face of the material. A plurality of detectors, placed on the side of the material opposite the laser, supplies the material transmittance information to a microcomputer for calculating the moisture or filler content of the material. When thin dielectric materials and/or continuous scanning are utilized the submillimeter laser is pumped by a single CW (continuous wave) $CO_2$ laser and when thicker dielectrics are measured with discrete pulses the submillimeter laser is pumped by a single TEA (Transversely Excited Atmospheric) $CO_2$ laser. Depending on the transmission properties of the environment in which the apparatus operates, either the submillimeter laser beam or the infrared pump laser beam can be transmitted through the medium surrounding the apparatus in order to minimize pre-measurement attenuation of the beam.

8 Claims, 6 Drawing Sheets

SUBMILLIMETER LASER MEASUREMENT OF WATER OR FILLER CONTENT OF SHEETS AND BANDS OF DIELECTRIC MATERIAL

RELATED APPLICATION

This application is a continuation-in-part of pending application Ser. No. 730,734 filed May 6, 1985.

BACKGROUND OF THE INVENTION

1. Field of the Invention

This invention is addressed to measurement and control of the water or filler content of sheets and bands of dielectric materials such as sheet materials including paper, plastics, textiles and wood veneers, the water content measurement of bands of filamentary material such as plastic and textile fibers and the water content measurement of food and agricultural products during pre-storage processing. Measurement and control of water content is of primary importance in the manufacture of sheet materials such as paper and plastics. The same basic technique can also be used for fillers which are added to improve strength or other qualities. Although the following discussion is framed mostly in terms of water content, it is also applicable to the measurement of such fillers.

2. Discussion of Background

In order to establish the utility of a particular water content measuring apparatus, it is necessary for the particular apparatus to display a wide range of water content which it can accommodate and to provide a further wide range with respect to the kind of dry stock which it can accommodate. Other important characteristics of the apparatus which is used for measuring water content include the sensitivity to non-moisture related stock characteristics, the spatial resolution and the ease and speed with which the material can be scanned.

Prior art attempts at measuring and controlling the humidity and moisture are contained in, for example, "Humidity and Moisture: Measurement and Control in Science and Industry", Volume II, Section II, Editors, A. Wexler & E. J. Amdur, Symposium Proceedings, Reinhold Publishing Corporation, New York Library of Congress #65-13613 (1965) and in the "Paper Industry Instrumentation", J. R. Lavigne Miller Freeman Publishers, San Francisco, 1977, Chapter 10. These techniques usually employ either infrared radiation or microwaves. Each of these prior art techniques of water measurement in various materials has the disadvantage that it has either a limited range of water content which can be accommodated or a limited range of materials which it can accommodate, or both. Furthermore, the sensitivity to other characteristics, the spatial resolution and the ease and speed with which the materials can be scanned are all problems with the prior art devices.

Many dielectric materials are nearly transparent to microwaves, but with microwaves it is difficult to make multi-wavelength measurement. Multi-wavelength measurements can be effected in the infrared spectrum, however, the dielectric sheets may be quite opaque and thus it is often necessary to make reflection rather than transmission measurements. The measurement of reflection is inherently a more difficult problem than the measurement of transmission. Also, attenuation and diffusion of infrared radiation due to scattering is a serious problem.

The use of microwaves to measure moisture content is disadvantageous because the microwaves are too long to permit spatial resolution on a millimeter scale. This millimeter resolution is the extent required in many industrial applications. Although microwave devices can handle a broad range of moisture content, they are quite insensitive at low moisture levels. Infrared devices provide good precision at low moisture levels but their use is restricted to such levels, usually less than 10% moisture content.

One approach used in the prior art to develop a moisture type gauge is represented by the U.S. Pat. No. 3,851,175 to Dahlin wherein a moisture gauging apparatus is provided which includes a tungsten light source having a filament voltage source capable of remote adjustment. The light source is capable of supplying radiation in both the 1.8 and 1.9 micron wavelength bands. The radiation from the source is collimated by an optical system and provides a beam of radiation containing both a first spectral band of radiation lying outside but near an absorption band of water and a second spectral band of radiation that lies within the absorption band of water. This radiation beam containing both spectral bands is directed onto paper where the moisture content is to be determined. A receiver is provided for detecting the radiation, either transmitted through the paper or backscattered from the paper and the information received is converted into an electrical signal indicative of the ratio of the energy received in the bands. A signal is also supplied for indicating the opacity of the paper which is combined with the ratio indication signal to provide a compensated moisture reading.

This type of device employed by Dahlin, which employs two wavelengths isolated by filters to correct moisture measurement for the variation in other sheet properties is confined to low moisture levels and light stock paper which is of course limiting in not only moisture level but also in the kind of materials which can be examined. It is also to be noted that this multi-wavelength example provides for the necessity for making reflection rather than transmission measurements.

There has been a recent attempt to provide for thin paper sheet moisture measurements using a submillimeter laser as described in "Paper Sheet Moisture Measurements in the Far Infrared" Conference Digest, Eighth International Conference on Infrared and Millimeter Waves by Boulay et al., December, 1983. These theoretical discussions were confined to the use of a single wavelength metallic guided-wave $CH_3OH$ laser with hole coupled end mirrors which were pumped with a $CO_2$ laser whereby the output of the laser was directed at normal incidence onto a paper sheet. This theoretical discussion provided only a measurement for normal incidence on a thin paper sheet with a quasi continuous wave laser (CW) output and is unable to take into account the changing conditions with respect to sheet and band dielectric materials other than thin paper and is thus limited with respect to solving the other problems discussed above. Another disadvantage of this approach is that the hole coupled end mirror arrangement used on the output of the $CH_3OH$ laser prevents the laser output from being confined to a well-collimated beam which can be directed onto a small area of the material. Furthermore, the diffused nature of the hole coupled mirror output makes it difficult to use for scanning across a width of material.

SUMMARY OF THE INVENTION

Accordingly, it is one object of the invention to provide an apparatus which can provide for the measurement and thus the control of water content of varying widths of diverse sheet materials including textiles, plastics and wood veneers, bands of filamentary materials, as well as food and other diverse agricultural products.

It is also an object of the present invention to provide a water content measuring apparatus which has a wide range of sensitivity with respect to the range of water content being measured, the range of the sheet materials which can be accommodated, the insensitivity to non-moisture related stock characteristics, greatly reduced scattering, improved spatial resolution and ease and speed of scanning of moving sheets of wide dielectric materials.

It is also an object of the present invention to provide a measuring apparatus for the filler content of paper, plastics and other dielectric materials in the form of sheets or bands.

The objects of the present invention are attained by utilizing a submillimeter laser (SMM) whose beam is repeatedly swept over a preprogrammed path onto a dielectric sheet or band having a plurality of detectors located on the side of the dielectric opposite the laser to provide for multiple measurements of the transmission of the sample as the beam pattern is scanned along the width of the moving sample.

It is another object of the present invention to provide for measurements of the moisture content of thin dielectric materials such as newsprint and light textiles by utilizing a frequency stabilized CW (continuous wave) $CO_2$ pumping laser in combination with the submillimeter laser.

It is another object of the invention to provide a TEA-$CO_2$ (Transversely Excited Atmospheric Laser) as a pumping laser in conjunction with the submillimeter laser (SMM) which is utilized in order to provide for scanning of heavy materials such as cardboard, heavy paper, plywood, wood veneer, thick plastics and heavy textiles.

BRIEF DESCRIPTION OF THE DRAWINGS

A more complete appreciation of the invention and many of the attendant advantages thereof will be readily attained as the same becomes better understood by reference to the following detailed description when considered in connection with the accompanying drawings, wherein.

DETAILED DESCRIPTION OF THE PREFERRED EMBODIMENTS

Figure 1:
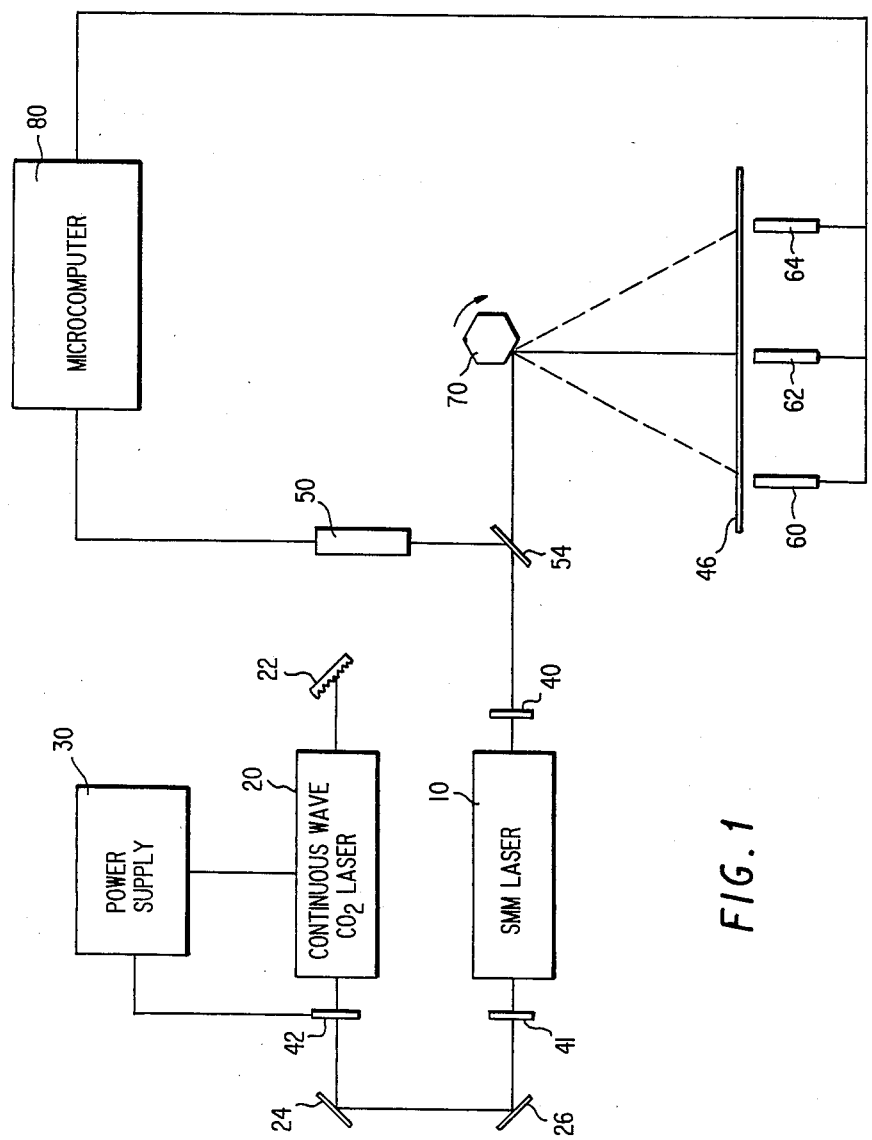
FIG. 1 is a block diagram of a first embodiment of the moisture measuring apparatus of the present invention.

Referring now to the drawings, wherein like reference numerals designate identical or corresponding parts throughout the several views, and more particularly to FIG. 1 thereof, there is illustrated an apparatus which performs a moisture or filler content testing operation on a sheet or band of dielectric material 46 such as for example newsprint, fine paper, thin plastic, light textile or textile filaments. A SMM (submillimeter) CW laser 10 is repeatedly swept over a preprogrammed path on the sample 46 by the rotation mirror 70. The mirror 70 may have its axis wobbled in order to perform a predetermined tracing pattern on the material 46 such as a circular or other pattern. Alternately, the sample and/or the laser can be moved mechanically to scan the desired pattern on the sample. If the sample is normally in motion perpendicular to the FIG. 1 (i.e., moving out of the drawing toward the viewer) such as a sheet or band emerging from a production machine, the total beam scan pattern can be accomplished by using auxiliary optical or mechanical scanning in the direction normal to the sheet motion. Beam steering by means of a scanning mirror or other optical element has the inherent advantage that only a small mass must be moved mechanically and the scan can therefore proceed rapidly.

Figure 5:
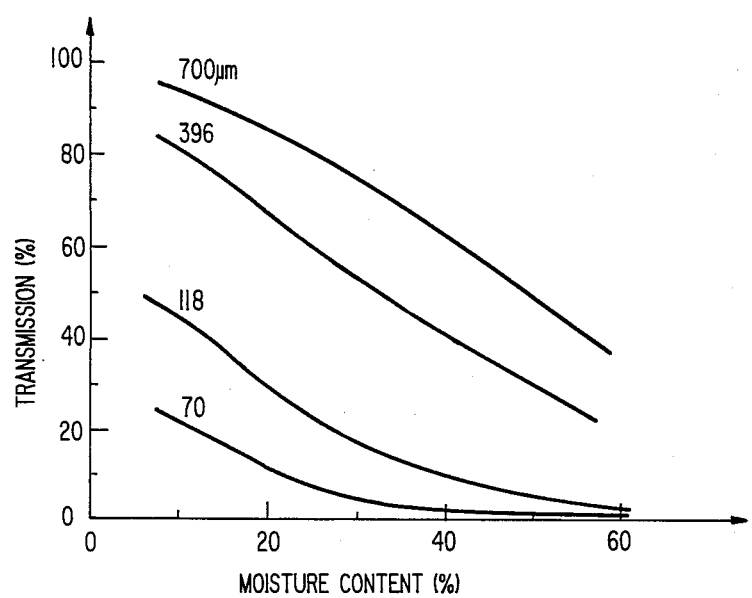
FIG. 5 is a set of typical transmittance curves as a function of water content for newsprint.

The detector 50 monitors the power output of the SMM laser 10 as sampled by the beam splitter 54 while the array of detectors 60, 62 and 64 measure the transmission of the sheet or band as the beam pattern is scanned. The transmittance is defined as the ratio of the intensity transmitted by the sheet (detectors 60, 62 and 64) to the incident intensity (detector 50). A microcomputer 80 calculates and stores beam position and transmittance data. The microcomputer also performs the calculations necessary to determine water content from the transmittance measurements, using previously measured calibration curves. Typical transmittance curves for newsprint are shown in FIG. 5. The procedure with respect to the calculation based on the transmittance data is evident to those versed in the art. This data can be displayed in a variety of different forms and/or fed directly to process control devices.

The SMM laser 10 is optically pumped with a frequency stabilized CW (continuous wave) $CO_2$ laser in the embodiment of FIG. 1. This CW laser provides for a continuous scanning output from the SMM laser 10 and also provides for precise intensity and frequency control in the output of the SMM laser 10. The construction of the CW-$CO_2$ laser provides maximum mechanical and thermal stability and precise frequency stability is achieved by mounting the output coupler 42 on a piezoelectric crystal which is servo controlled. Hybrid mirrors 40 and 41 admit the $CO_2$ pump radiation, let the submillimeter laser output exit and maintain the beam-structure and quality of the output of the laser 10. These hybrid mirrors 40 and 41 consist of a metallic grid of dimensions appropriate for SMM reflection applied over a dielectric film structure appropriate for 10 micron ($CO_2$) reflection, with both being supported by a transparent crystal.

The frequency stabilized CW type $CO_2$ laser 20 optically pumps the submillimeter laser 10, via plane mirrors 24 and 26, and is tuned by rotating the diffraction grating 22 to operate on any one of a large number of output wavelengths. The choice of a particular wavelength, together with the choice of gas to be employed in the submillimeter laser 10 determines the wavelength of the submillimeter output. The CW $CO_2$ laser 20 is powered by the CW $CO_2$ laser power supply 30. The continuous wave $CO_2$ laser 20 is well developed and readily available on the commercial market. The submillimeter waveguide laser 10 is a device consisting of a quartz or metallic tube, in which the selected gas is placed and is closed on each end by an appropriate window. The input window must be transparent to $CO_2$ laser radiation and the output window must be transparent to the submillimeter radiation. Alternatively the hybrid mirrors 40 and 41 described previously can serve as windows. The submillimeter laser action is achieved by introducing the correctly tuned laser beam from the output of the continuous wave $CO_2$ laser 20 into the submillimeter laser 10. No other electrical or other excitation of the laser 10 is required. The detectors 50, 60, 62 and 64 are pyroelectric detectors which are commercially available and are formatted as a single element, in linear arrays or in square arrays. Other appropriate detectors may be used.

Figure 4A:
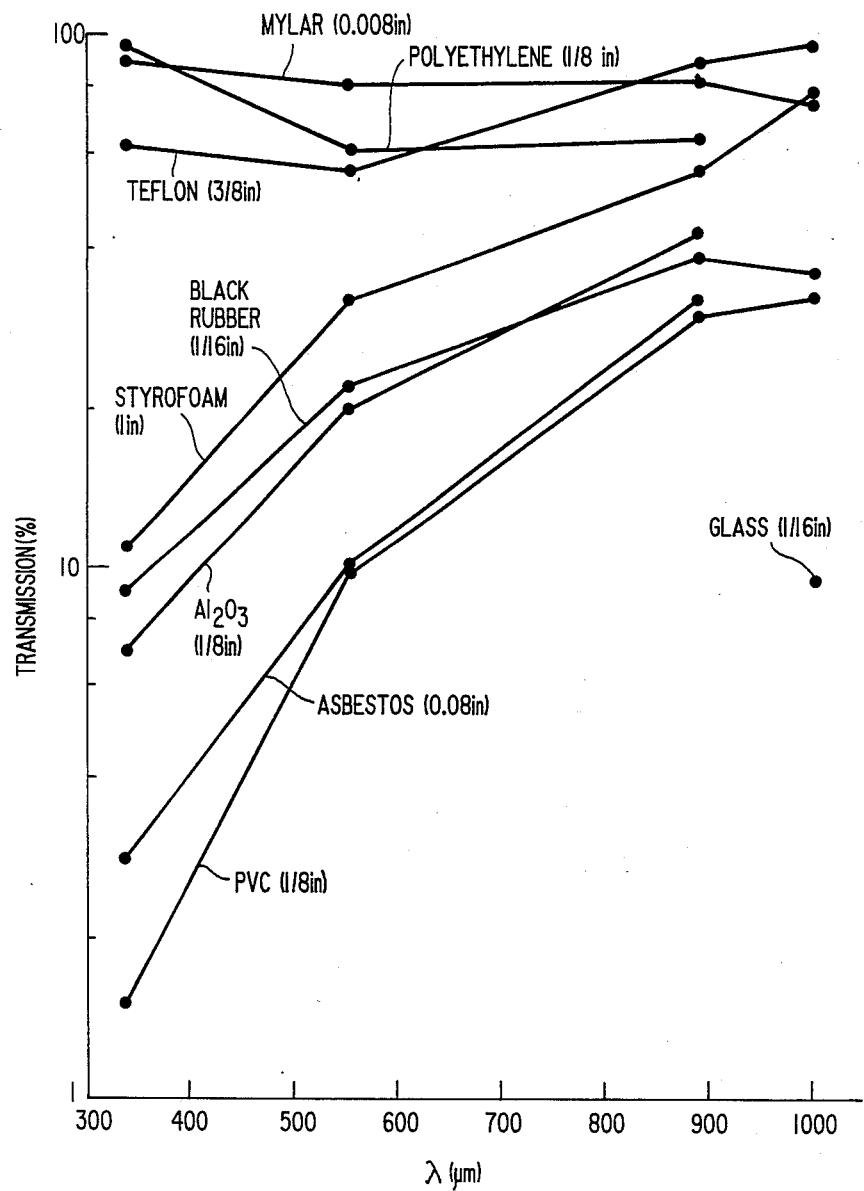
FIGS. 4a and 4b are graphs of submillimeter wavelength transmission of common dielectric materials.
Figure 4B:
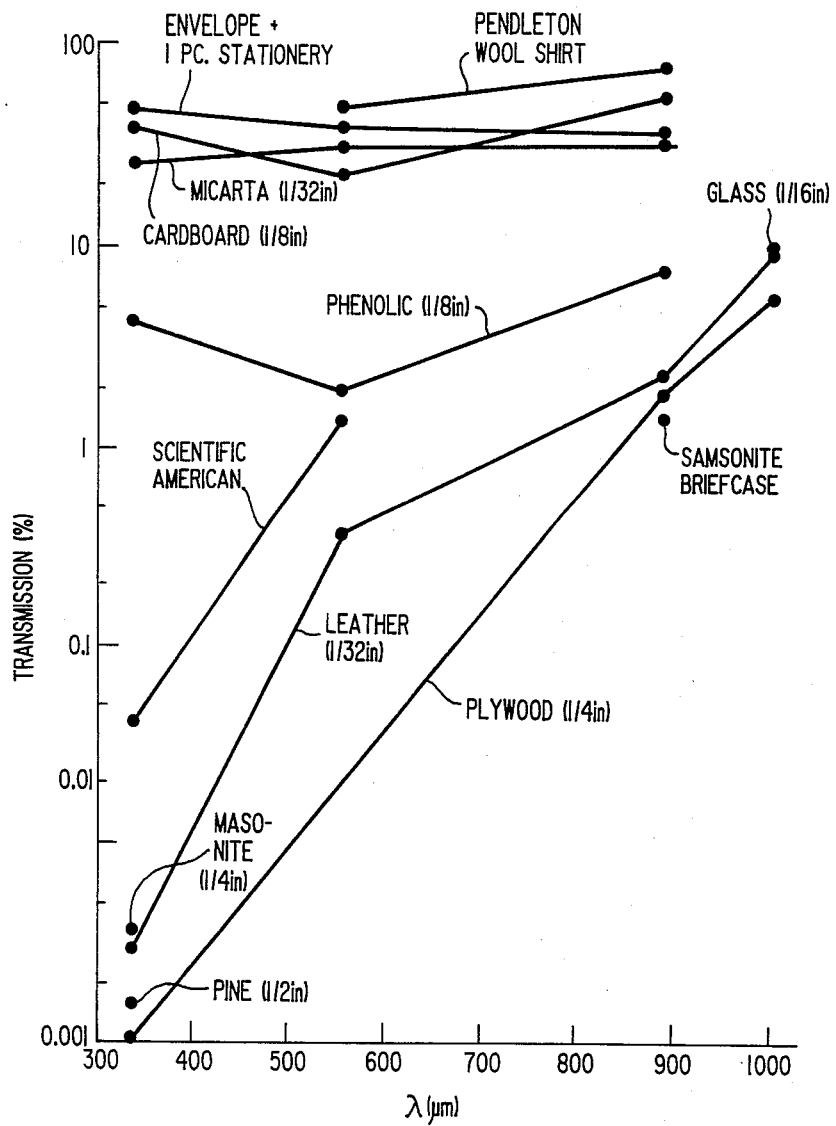

The selection of the use of submillimeter lasers for the measurements is based upon the consideration that many common dielectric materials are quite transparent in the submillimeter region of the electromagnetic spectrum, which for present purposes we define as comprising wavelengths from approximately 50 to 1,000 microns. The FIGS. 4a and 4b present a graphic illustration of the transmittance of submillimeter waves through various dielectric materials. It is also to be noted that this particular spectral region of from 50 to 1,000 microns is characterized by strong absorption in water with a strong but simple wavelength dependence. Thus the transmittance of submillimeter waves through various dielectric sheets is very sensitive to small amounts of water.

Submillimeter waves are also utilized because they represent an optimum compromise in spatial resolution (i.e., the precision with which the spatial variation of moisture content throughout the sheet can be measured). In this area there are two important factors. Unlike other sources, the laser produces a highly directional beam which can be steered to any desired point. It is also important that the minimum area which can be examined is determined by the wavelength of the radiation and cannot be smaller in diameter than the wavelength. Variations on the scale of a millimeter can thus be measured with a submillimeter laser. The use of microwaves, as in the prior art, is too restrictive in the sense that the microwaves are too long to permit millimeter resolution. Millimeter resolution is approximately the limit required in many industrial applications. An even more important aspect of the comparison with infrared devices is that scattering by the sheet material is much weaker for submillimeter than for infrared waves. As a consequence it is easier to be certain that the whole beam is collected and thus increase the accuracy of the measurements. Moreover, nearly all of the beam attenuation is due to absorption by water, and it is therefore unnecessary to make a correction for scattering. Such corrections are often both difficult and imprecise.

The use of submillimeter waves also present a distinct advantage in terms of the range of moisture content which can be accommodated with high precision. On the other hand microwave devices, while able to handle a broad range of moisture content, are quite insensitive at low moisture levels. Likewise infrared devices, while providing good precision at low moisture levels, are necessarily restricted to such low moisture levels. Because of the intermediate absorption by water, the good transparency of dry stock materials, low scattering, and the high spatial resolution, submillimeter waves combine the best features of each of the other spectral regions. Submillimeter waves are much more strongly transmitted by paper than infrared waves. Consequently, a wider range of dry stock including liner board and other heavy paper products can be accommodated.

Submillimeter waves are only very weakly scattered by the cellulose content of the paper and hence no empirical correction for scattering need be made, as must be done for infrared gauges. Submillimeter waves are strongly absorbed by water and thus provide a basis for precise measurement of water content. Our measurements indicate that measurements with a precision better than 1% can be made for newsprint containing up to at least 50% water by weight. By comparison to microwave gauges, much better spatial resolution can be obtained at submillimeter wavelengths, and more accurate determination of the moisture profile across the sheet can therefore be achieved. A submillimeter gauge can also produce much greater accuracy in water content measurements at low moisturelevels than a microwave device. Some typical transmission versus water content measurements made on newsprint at several submillimeter wavelengths are plotted in FIG. 5.

Powerful optically pumped lasers which operate at many different submillimeter wavelengths have recently been developed, and their use makes the development of a practical submillimeter paper moisture gauge possible. In addition to the advantages listed above, the laser produces a well-defined beam which can be scanned across the sheet by optical means. Neither the microwave nor the infrared type gauges are able to produce a beam in which the radiation is confined and which can be steered, as a laser beam can be. As a result of all these considerations a submillimeter laser gauge has the potential to provide superior performance in terms of speed, accuracy, high spatial resolution, wide range of moisture content and wide range of dry stock paper material.

Figure 2:
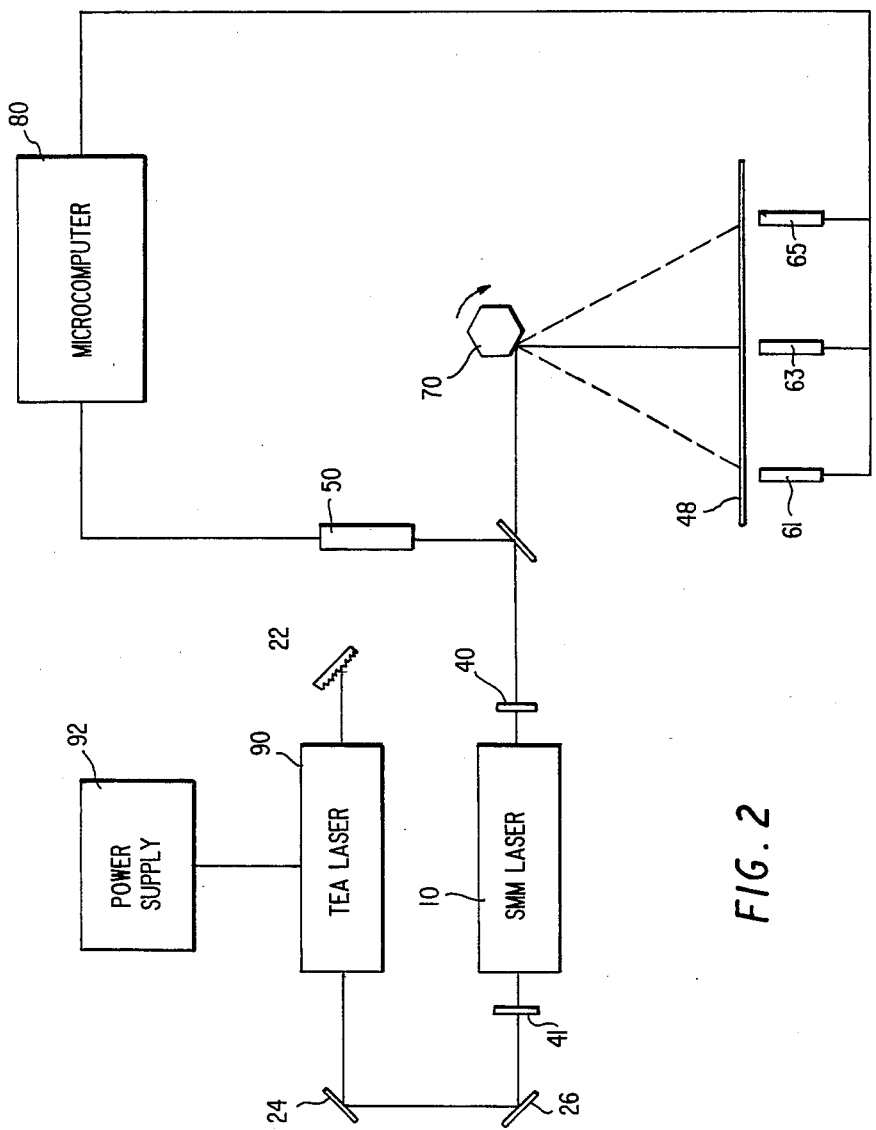
FIG. 2 is a block diagram of a second embodiment of the present invention.

The embodiment of FIG. 2 is directed to a structure which can provide for moisture content measurement of a material 48 fitting into a category of heavier materials than the material 46 of the FIG. 1 embodiment. For example, utilizing the structure of FIG. 2, heavy paper, cardboard, plywood, wood veneer, thick plastics and heavy textiles can be scanned for moisture content. In order to accomplish the measurement of these heavier dielectric materials the FIG. 2 embodiment utilizes a TEA-$CO_2$ (Transversely Excited Atmospheric laser) 90 which provides for enhanced signal strength from the output of the SMM laser 10, over that of the FIG. 1 embodiment, and therefore provides for more penetration which is necessitated by the heavier material 48. The TEA-$CO_2$ (Transversely Excited Atmospheric laser) 90 also provides simultaneous multiple wavelengths to be output from the SMM laser 10.

Thus, aside from providing for enhanced signal strength by using a TEA laser 90 as the pumping laser for the SMM laser 10, it also enables simultaneous output of multiple wavelengths which can be used to discriminate effects on the transmittance due to other sheet properties, because the change in water transmittance as a function of wavelength is known. Thus utilizing the structure of FIG. 2, with an appropriate TEA laser power supply 92, multiple wavelengths will be output from the submillimeter laser 10 and can be used in the manner indicated above to discriminate the effects due to other sheet properties because of the known relationship between the change in water transmittance and the wavelength. It is for this reason that the detectors 61, 63 and 65 can be constructed as individual detectors which effectively sample the transmittance at each of the two wavelengths output from the laser 10 on alternate successive pulses when using a TEA pumping laser 90. That is, if each of the detectors 61, 63 and 65 is only a single detector, one of the two wavelengths that are always present in the SMM laser output can be blocked from the detector by switching appropriate filters in front of the detector for successive pulses. The control of the filters to provide the required sampling is itself well known and can be accomplished in a variety of ways such as a simple switch arrangement controlled by the microcomputer. Of course more than two wavelengths may be used and furthermore the corresponding detectors would also therefore sample in corresponding alternations of more than two corresponding frequencies.

It should be noted that the TEA-$CO_2$ laser produces a series of discrete pulses rather than a continuous wave and therefore will not produce a continuous scan pattern. The pulse repetition rate can be several hundred Hz, so that the moisture content can be sampled every few milliseconds.

The detectors 61, 63 and 65 could also be formed as a plurality of detector units for each of the detectors 61, 63 and 65. In other words the detector 61, for example, could actually comprise two detector units, one dedicated to a first wavelength output by the laser 10 and the other dedicated to a second wavelength output from the laser 10. Appropriate filters placed in front of the detectors can function to provide the proper wavelength to each of the detectors. Likewise, as indicated above, three or more detector units for each of the labeled detectors 61, 63 and 65 could be used if more than two wavelengths are generated by the laser 10 acting in conjunction with the TEA pumping laser 90.

While earlier attempts to exploit the submillimeter wave transparency of dielectrics in order to inspect objects surrounded by such materials have been frustrated by the presence of water, the present invention provides the use of lasers to actually locate the water itself in the dielectric sheet and band materials and to measure its concentration.

Either the CW $CO_2$ laser 20 of FIG. 1 or the TEA-$CO_2$ laser of FIG. 2 provide the optical pumping for the SMM laser 10 in such a manner that the grating 22 provides the tuning to operate on any one of a large number of output wavelengths. The choice of this wavelength, together with the choice of the gas to be employed in the submillimeter laser, determines the wavelength of the submillimeter output. Several possible combinations which produce strong laser outputs are listed in the Table 1 below. Note that for some pump wavelengths produces by TEA-$CO_2$ type lasers, there are strong multiple submillimeter laser lines produced.

TABLE 1

| | | SMM output wavelength | |
|---|---|---|---|
| SMM laser gas | $CO_2$ pump line | CW—$CO_2$ pump | TEA—$CO_2$ pump (multiple wavelengths only) |
| $CH_3OH$ | 9P34 | 70 $\mu m$ | |
| $CH_3OH$ | 9P36 | 118 | |
| $CH_3OH$ | 9P14 | | 142 and 58 $\mu m$ |
| HCOOH | 9R18 | 393 | |
| HCOOH | 9R18 | 420 | |
| $CH_3OH$ | 9P12 | | 452, 164, 46 |

TABLE 1-continued

| | | SMM output wavelength | |
|---|---|---|---|
| SMM laser gas | $CO_2$ pump line | CW—$CO_2$ pump | TEA—$CO_2$ pump (multiple wavelengths only) |
| $CH_3F$ | 9P20 | 496 | |
| $CH_3OH$ | 9P16 | 570 | 570, 118 |
| $^{13}CH_3F$ | 9P32 | 1220 | |

Figure 3:
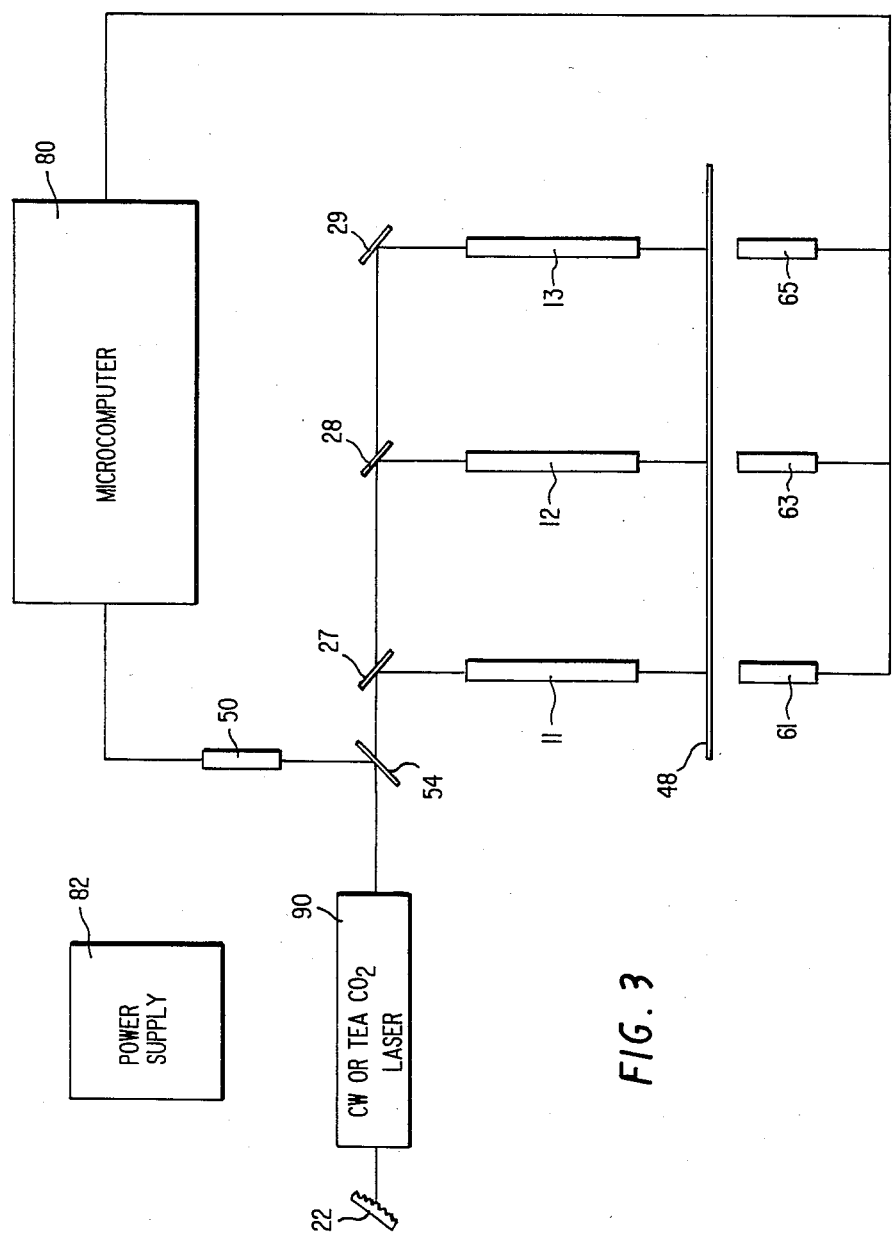
FIG. 3 is a block diagram of a third embodiment of the present invention.

The embodiment of FIG. 3 is directed to a structure which can provide moisture measurement in a sheet material 48 in a factory environment where the air is contaminated with water or other substances which would attenuate the SMM laser beam before it reaches the material to be measured. It provides a multiplicity of submillimeter lasers 11, 12, 13 located close to the material sheet 48. The pump beam from the $CO_2$ laser 80, which can be either a CW or a TEA laser depending on the material to be measured, is directed into the submillimeter lasers by a series of partially reflecting mirrors. The reflectance of the successive mirrors 27, 28, 29 is graded so that pump beams of equal intensity are delivered to the submillimeter lasers. In this embodiment the submillimeter laser beams pass through only a short length of factory air, whereas the $CO_2$ pump laser, whose beam is not attenuated by air moisture, can be placed at a more remote location.

Obviously, numerous (additional) modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An apparatus for measuring the moisture content of a sheet or band of dielectric material, comprising:
    at least one submillimeter laser pumped by a single $CO_2$ laser for outputting a beam of submillimeter wavelength radiation;
    means for scanning said beam across the width of one face of said sheet or band;
    detector means positioned opposite said sheet or band from said beam for receiving the portion of said scanning beam which is transmitted through said sheet or band and for outputting transmittance signals;
    processing means for receiving said transmittance signals and for calculating the moisture content of said sheet or band wherein the spatial distribution of water content within said sheet or band of dielectric material can be measured with a maximum spatial resolution of approximately 1 millimeter.

2. The apparatus of claim 1 using a CW laser, wherein said material is paper and including means for measuring the water content continuously in real time.

3. The apparatus of claim 2, wherein said detector means measures the water content of paper for the range of 1 to 50% of the dry basis weight of the paper.

4. The apparatus of claim 1 using a pulsed laser, wherein means are provided for sampling the water content every few milliseconds when said sheet or band of dielectric material is a heavy sheet material.

5. The apparatus of claim 1 using a pulsed laser, wherein said pumped submillimeter laser produces two submillimeter wavelengths simultaneously and for discrimination against a background signal or for measurement of a second component.

6. An apparatus for measuring the moisture content of a sheet or band of dielectric material comprising:
- a submillimeter laser pumped by a single $CO_2$ laser for outputting a beam of submillimeter wavelength radiation;
- means for scanning said beam across the width of one face of said sheet or band;
- detector means positioned opposite said sheet or band from said beam for receiving the portion of said scanning beam which is transmitted through said sheet or band and for outputting transmittance signals;
- processing means for receiving said transmittance signals and for calculating the moisture content of said sheet or band.

7. An apparatus for measuring the filler content of a sheet or band of dielectric material, comprising:
- at least one submillimeter laser pumped by a single $CO_2$ laser for outputting a beam of submillimeter wavelength radiation;
- means for scanning said beam across the width of one face of said sheet or band;
- detector means positioned opposite said sheet from said beam for receiving the portion of said scanning, beam which is transmitted through said sheet and for outputting transmittance signals;
- processing means for receiving said transmittance signals and for calculating the filler content of said sheet or band of material.

8. An apparatus for measuring the moisture content of a sheet or band of dielectric material comprising:
- a single $CO_2$ laser outputting a pump beam;
- at least one submillimeter laser positioned in the vicinity of said dielectric material;
- means for directing said pump beam from said $CO_2$ laser onto said at least one submillimeter laser wherein the intensity delivered to each of said at least one submillimeter lasers is equal;
- detector means positioned opposite said sheet or band from said at least one submillimeter laser for receiving the portion of the outout of each of said at least one submillimeter laser which is transmitted through said sheet or band and for outputting transmittance signals;
- processing means for receiving said transmittance signals and for calculating the moisture content of said sheet or band;
- wherein the positioning of said at least one submillimeter laser in the vicinity of said dielectric material provides for an accommodation of moisture or pollution in the air surrounding said sheet or band so as to avoid attenuation of submillimeter wavelength radiation output from said at least one submillimeter laser.

* * * * *